US00PP25191P3

(12) United States Plant Patent
Layt

(10) Patent No.: US PP25,191 P3
(45) Date of Patent: Dec. 30, 2014

(54) ***GREVILLEA JUNIPERINA* PLANT NAMED 'H22'**

(50) Latin Name: *Grevillea juniperina*
Varietal Denomination: H22

(71) Applicant: Todd Layt, Richmond (AU)

(72) Inventor: Todd Layt, Richmond (AU)

( * ) Notice: Subject to any disclaimer, the term of this patent is extended or adjusted under 35 U.S.C. 154(b) by 296 days.

(21) Appl. No.: 13/573,866

(22) Filed: Oct. 10, 2012

(65) Prior Publication Data

US 2014/0101809 P1 Apr. 10, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Sam McCoy, Jr.

(57) ABSTRACT

'H22' is a distinctive variety of *Grevillea juniperina* which is characterized by a very short mature plant height combined with a prostrate and dense growth habit.

1 Drawing Sheet

Latin name of the genus and species: The Latin name of the genus and species of the novel variety disclosed herein is *Grevillea juniperina*.

Variety denomination: The inventive variety of *Grevillea juniperina* disclosed herein has been given the variety denomination 'H22'.

The present application claims priority from a provisional U.S. application No. U.S. 61/545,620 filed Oct. 11, 2011, which is herein incorporated by reference.

BACKGROUND OF THE INVENTION

The present invention relates to a new and distinct perennial variety of *Grevillea juniperina*, which has been given the variety denomination of 'H22'. Its market class is that of an ornamental groundcover plant. 'H22' is intended for use in landscaping and as a decorative plant.

Parentage: The *Grevillea juniperina* variety 'H22' was finally selected in 2008 in an Australian nursery in the state of New South Wales following a selection process carried out from 2005 to 2008 involving a large group of open pollinated seedlings of prostrate yellow (common form) *Grevillea juniperina* (unpatented and unnamed) production stock. In 2005, eight open-pollinated candidate seedlings were identified as having a substantially shorter plant height and improved vigor by comparison to the maternal parent plant and were isolated for further evaluation. After two additional years of evaluation, the trial was narrowed to two selections in 2008. 'H22' was selected from the remaining two candidate plants due to its very short mature plant height combined with a prostrate and dense growth habit.

An application for plant breeders' rights for variety 'H22' has been lodged with the Australian Plant Breeders' Rights Office, and was first gazetted in 27 Mar. 2006 under Application No. 2006/036.

Asexual Reproduction: 'H22' was first propagated asexually by division in the state of New South Wales, Australia in 2008 and has since been asexually propagated by division for four successive generations. The distinctive characteristics of the inventive 'H22' variety are stable from generation to generation; plants of the variety produced by asexual reproduction maintain the distinguishing characteristics of the original plant.

'H22' has a short plant height and a prostrate, spreading growth habit whereas prostrate (common form) yellow *Grevillea juniperina* (unpatented and unnamed) has a medium plant height and semi erect growth habit.

SUMMARY OF THE INVENTION

'H22' is a distinctive variety of *Grevillea juniperina* which is characterized by a very short mature plant height combined with a prostrate and dense growth habit.

BRIEF DESCRIPTION OF THE FIGURES

The FIGURE shows a mature 'H22' plant with another candidate plant from the original selection work. Of note are the short plant height and dense habit of 'H22'.

BOTANICAL DESCRIPTION OF THE PLANT

The following is a detailed botanical description of a new and distinct variety of *Grevillea juniperina* known as 'H22'. Unless indicated otherwise, the descriptions disclosed herein are based upon observations made in September 2011 of mature 'H22' plants (approximately 12 months old) grown in 200 mm nursery pots from rooted cuttings with soilless potting media, maintained with granular slow release fertilizer, and regularly watered with overhead irrigation. No pest and disease measures were taken.

Those skilled in the art will appreciate that certain characteristics will vary with older or, conversely, younger plants. 'H22' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 2001 edition. Note that generic color descriptions such as 'white' do not exist in the RHS charts and the corresponding RHS colors are quoted.

TECHNICAL DESCRIPTION OF THE VARIETY

Plant characteristics: 'H22' is a short plant forming a low and spreading habit. Average plant height is to 30 cm and average plant spread is 80 cm in a mature plant grown in a garden in Sydney, New South Wales, Australia.

Stems: Attitude is prostrate. Stem shape is cylindrical; texture is corky; Color of immature stems is yellow-green (144B) and mature stems are closest to greyed-orange (177A). Internode length averages 6.2 mm.

Leaf: Shape is linear lanceolate; apex is apiculate; margin is entire. Upper surface is glabrous and lower surface is pubescent. Average length is 10.2 mm and the average width is 1.8 mm. Color of the upper surface is green corresponding to RHS 137A and the lower leaf surface is yellow-green corresponding to 137C.

Roots: Clusters of closely spaced short lateral rootlets.

Inflorescence: Sessile racemes, terminal on short lateral branches.

Flowers: Perianth color is yellow-orange (RHS 16B); perianth tube width averages 3.7 mm with an average length of 21.6 mm, including the style. Style yellow-orange (16B); stigma green (144C); ovary green (144C); nectary yellow-orange (16B). Sepals not observed.

Fruit and seed: Observations not yet recorded.

Environmental tolerances: The winter hardiness of 'H22' is at least to USDA Zone 9a. 'H22' has heat tolerance typical of *Grevillea juniperina*. 'H22' has good drought tolerance typical of *Grevillea juniperina* once established.

Pest/disease resistance: No known insect pests. 'H22' has disease tolerance typical of *Grevillea juniperina*.

Cultural conditions: 'H22' is tolerant of a wide range of soil types and pH ranges.

COMPARISON OF 'H22' WITH OTHER VARIETIES OF *GREVILLEA JUNIPERINA*

While both 'H22' and 'Molonglo' have prostrate growth habits, the older branches of 'Molonglo' have a tendency to become decumbent, the older branches or 'H22' typically remain prostrate. 'H22' has a low plant height, reaching an average height of 30 cm whereas *Grevillea juniperina* 'Molonglo' can easily grow to be twice this size or larger to a height of 100 cm and a spread of 100 cm or more. Shorter internodes and a broader leaf give 'H22' a more dense foliage canopy by comparison with 'Molonglo'. The internode length of 'H22' is 6.2 mm on average whereas the typical internode length of 'Molonglo' ranges from 9 mm to 12 mm. Leaves of 'H22' are broader than those of 'Molonglo'; 'H22' has a leaf length-to-width ratio 5.67 whereas 'Molonglo' has a length-to-width ratio of approximately 9.33 (using the mean leaf length and width as described by the Australian Cultivar Registration Authority). As described by the Australian Cultivar Registration Authority, 'Molonglo' has an apricot flower corresponding to RHS Color Chart 1965 609/1 to 609/2 with a long red style whereas 'H22' has a distinctly yellow-green flower and style corresponding to RHS 16B.

The combination of its low height and dense, prostrate growth habit makes 'H22' a desirable ornamental plant suited for mass production for pot and landscape use.

That which is claimed is:

1. A new and distinct variety of *Grevillea juniperina* plant named 'H22', substantially as described and illustrated herein.

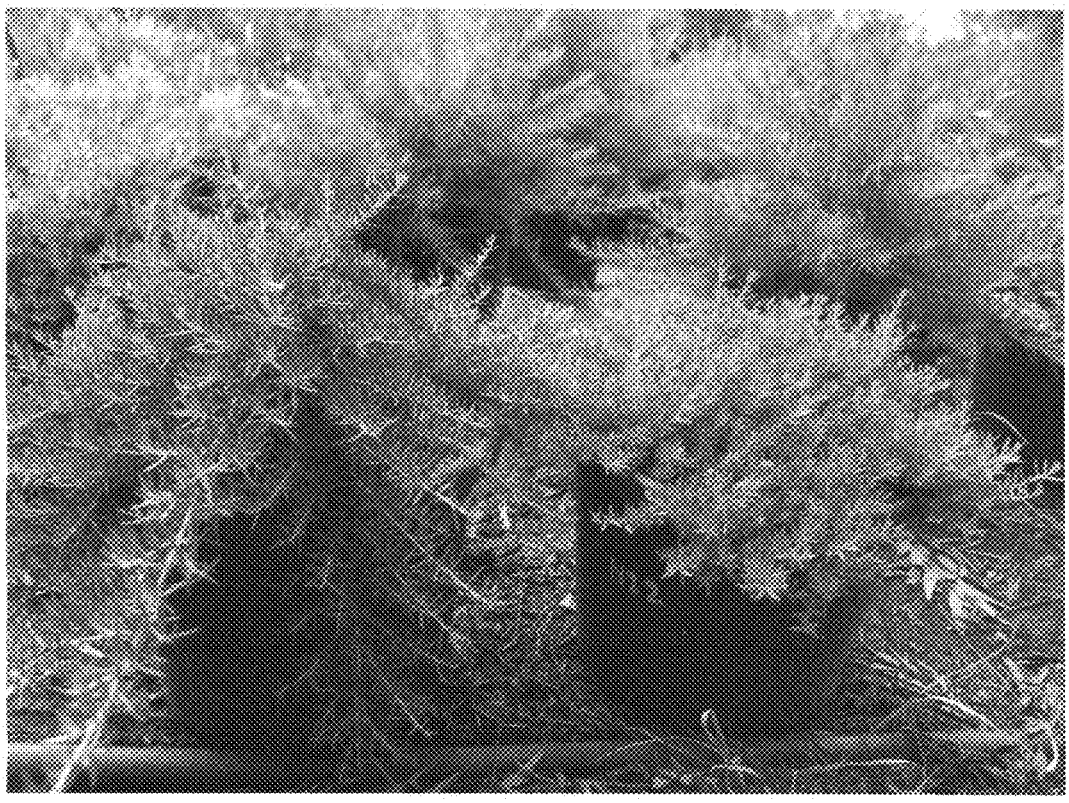

* * * * *